United States Patent [19]

Ryder et al.

[11] Patent Number: 4,784,637
[45] Date of Patent: Nov. 15, 1988

[54] ASEPTIC IRRIGATION SYRINGE

[75] Inventors: Francis E. Ryder, Arab; Rowland W. Kanner, Guntersville, both of Ala.

[73] Assignee: Ryder International Corporation, Arab, Ala.

[21] Appl. No.: 29,329

[22] Filed: Mar. 23, 1987

[51] Int. Cl.⁴ ............................................. A61M 1/00
[52] U.S. Cl. ...................................... 604/32; 604/35; 604/236; 604/248; 604/38
[58] Field of Search .................. 604/187, 38, 191, 236, 604/240, 246, 248, 249, 258, 30, 35

[56] References Cited

U.S. PATENT DOCUMENTS

| | | | |
|---|---|---|---|
| 1,831,668 | 11/1931 | Juhl | 604/248 |
| 2,485,842 | 10/1949 | Pennington | 128/214 |
| 2,842,124 | 7/1958 | James | 604/248 |
| 3,143,109 | 8/1964 | Gewertz | 604/236 |
| 3,157,201 | 11/1964 | Littmann | 137/625 |
| 3,323,774 | 6/1967 | Wilson | 604/248 |
| 3,747,812 | 7/1973 | Karman et al. | 604/236 |
| 3,780,736 | 12/1973 | Chen | 128/213 |
| 3,990,447 | 11/1976 | Vega | 128/234 |
| 4,082,095 | 4/1978 | Mendelson et al. | 128/235 |
| 4,187,849 | 2/1980 | Stim | 128/278 |
| 4,525,156 | 6/1985 | Benusa et al. | 604/30 |
| 4,553,964 | 11/1985 | Sasaki | 604/248 |
| 4,662,868 | 5/1987 | Cambio, Jr. | 604/38 |

Primary Examiner—Stephen C. Pellegrino
Assistant Examiner—Gene B. Kartchner
Attorney, Agent, or Firm—Trexler, Bushnell, Giangiorgi & Blackstone

[57] ABSTRACT

A flow control apparatus for providing selective fluid communication with physiological organs includes a nozzle structure for multiple conduits, a syringe having a fluid chamber for containing and discharging fluids in communication with the nozzle structure, two valve members having respective engaged surfaces relatively rotatable to provide valving action, and a clamp structure which forces the valve members together to establish fluid-tight seal between their engaged surfaces. The first valve member has a plurality of through apertures respectively communicating with separate fluid ports in the nozzle, and the second valve member has a through passageway communicating with the syringe chamber; the passageway is further selectively communicatable with at least one of the apertures in the first valve member to enable fluid flow between the respective nozzle port and the syringe chamber.

30 Claims, 3 Drawing Sheets

ASEPTIC IRRIGATION SYRINGE

BACKGROUND OF THE INVENTION

This invention relates to devices for controlling flow of fluid to and from physiological organs, for example, the bladder, and more particularly relates to valved control devices which enable selective irrigation and medication of organs.

In the effort to avoid infections and provide a generally closed system of multiple flow paths to enable selective irrigation and medication of organs, typically the bladder, multi-channel valve devices have been employed such as those devices described, for example in U.S. Pat. Nos. 3,990,447 and 4,082,095. In these described devices, a syringe is combined with a valved device for selecting from among multiple flow paths to enable separate medication, irrigation, and draining of fluid from the organ without disconnecting the syringe or the channel selector so that exposure to infection is reduced, particularly when repeated sequences of treatment of the organ are required.

SUMMARY OF THE INVENTION

In accordance with this invention a flow control apparatus for providing selective fluid communication with physiological organs includes a nozzle structure for multiple conduits, a syringe having a fluid chamber for containing and discharging fluids in communication with the nozzle structure, two valve members having respective engaged surfaces relatively rotatable to provide valving action and a clamp structure which forces the valve members together to establish fluid-tight seal between their engaged surfaces. The valve members can be fabricated from inexpensive ceramic material, for example high purity alumina, which enables the rotatable engaged surfaces to be ground to a highly polished finish and closely conforming flatness creating a fluid-tight seal under compression; the highly polished engaged surfaces can be relatively rotated without excessive resistance or frictional force during which the fluid-tight seal is maintained to prevent any accumulation of fluid between the engaged valve surfaces which could otherwise cause cross-contamination of different, sequentially flowing fluids. The first valve member has a plurality of through apertures respectively communicating with separate fluid ports in the nozzle, and the second valve member has a through passageway communicating with the syringe chamber; the passageway is further selectively communicatable with at least one of the apertures in the first valve member to enable fluid flow between the respective nozzle port and the syringe chamber.

The syringe can have a cylindrical body which houses both the syringe chamber and both of the valve members which are separated from the syringe chamber by an internal wall. A portion of the nozzle structure can also be received within the syringe housing, and the clamp structure secures the valve members between the internal wall and the nozzle structure to form a unitary assembly.

In a preferred embodiment, the clamp structure includes a resilient cushion engaging the first valve member and the cushion has a plurality of through passageways in fluid communication with the apertures of the first valve member. The second valve member can be cushioned by an O-ring seated on the internal wall. The nozzle structure can be secured within the syringe housing by a retaining ring which also maintains the cushion and the 0-ring under compression to seal the engaged surfaces of the valve members.

DESCRIPTION OF THE ILLUSTRATED EMBODIMENT

Figure 1:
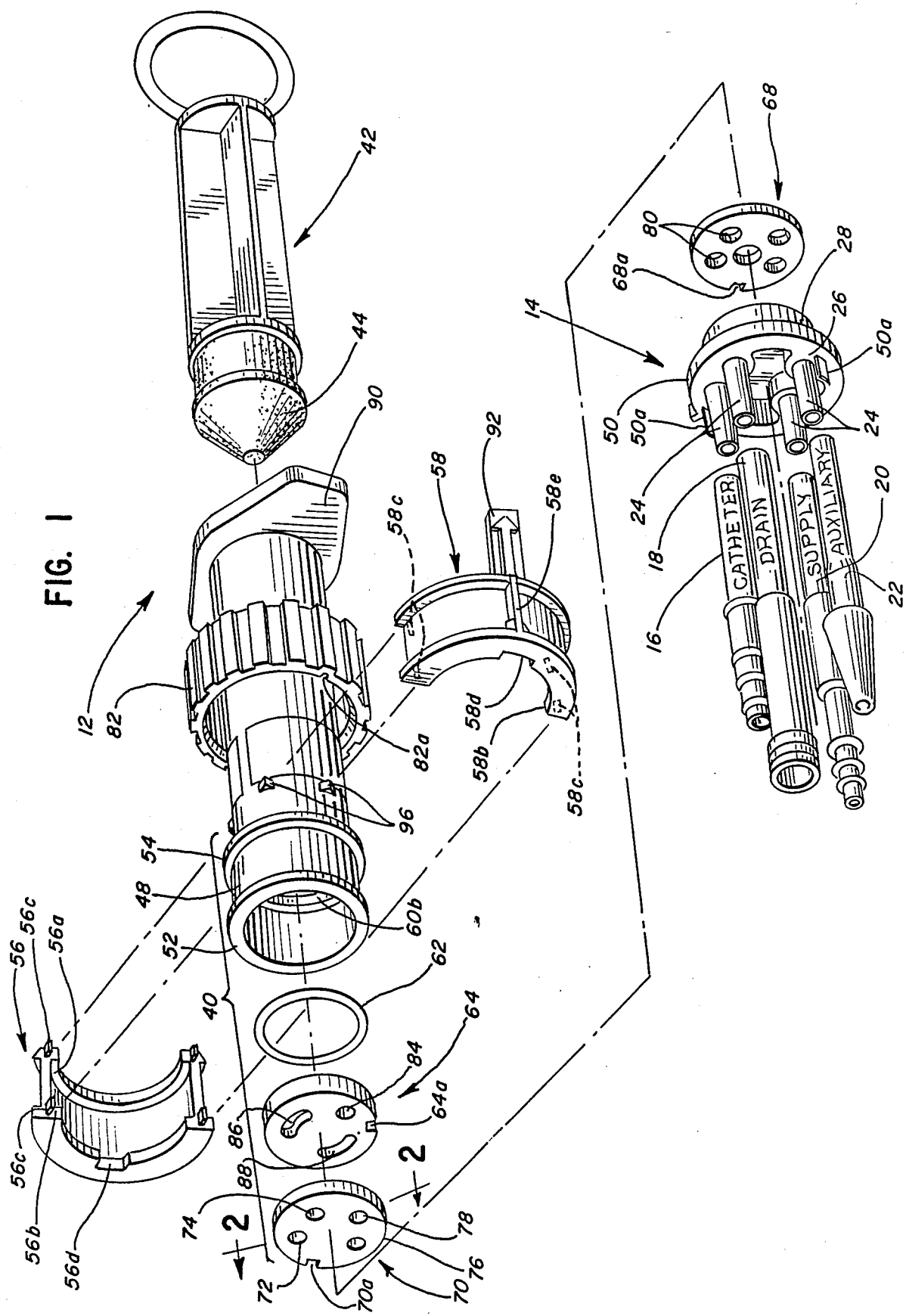
FIG. 1 is an exploded, perspective view of an embodiment of the flow control apparatus of the invention.

Referring to FIG. 1, an embodiment of the flow control apparatus is generally designated by reference character 10. The assembly 10 includes a syringe structure 12 and a nozzle structure 14 from which four separate tubes 16, 18, 20, and 22 are connected to provide multiple fluid conduits. The illustrated assembly 10 is particularly adapted for irrigative treatment of the bladder, in which tube 16 is labeled as the line leading to the catheter into the bladder (not shown); tube 18 is labeled as a drain line leading, for example, to a waste facility or to a device for obtaining a sample of the drain fluid for analysis. Tube 20 is a supply line leading from a source of irrigation solution, medication, or similar solution for delivery to the nozzle and therefrom to one of the other tubes, particularly the catheter line 16. Tube 22 is an auxiliary line available for connection to an alternate catheter or a second source of medication or the like. Each of the tubes 16, 18, 20 and 22 is connected to a respective one of four tubular nipples 24 projecting from the conduit end 26 of the nozzle structure 14

Figure 2:
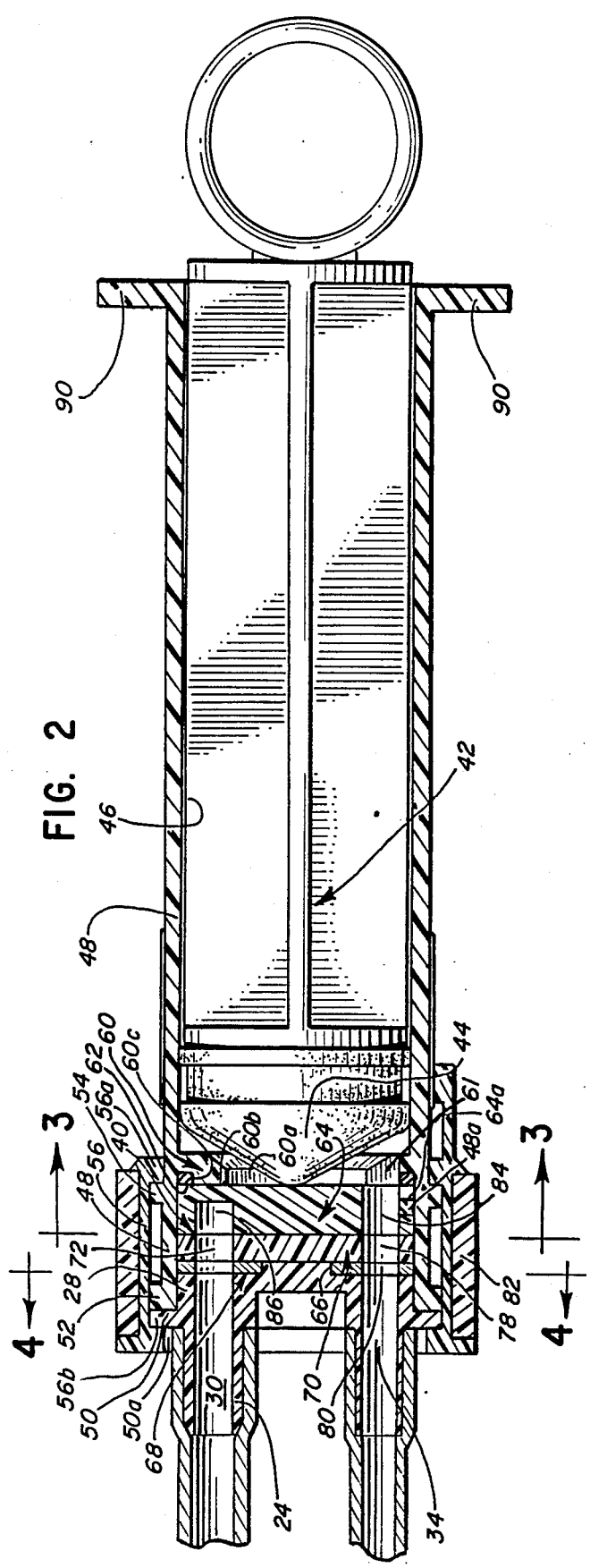
FIG. 2 is a sectional view taken along line 2—2 in FIG. 1 and in the indicated direction, illustrating the alignment of fluid flow conduits within the assembly.
Figure 4:
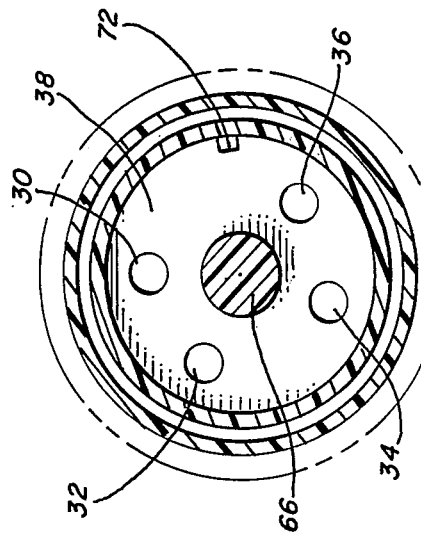
FIG. 4 is a sectional view taken along line 4—4 in FIG. 2 and in the indicated direction, illustrating the arrangement of flow conduits in a nozzle structure.

As shown in FIGS. 1 and 2, the nozzle structure 14 has a body 28 in the form of a solid cylinder prism through which four fluid flow bores 31, 32, 34, and 36 longitudinally pass, offset from the central axis as shown in FIG. 4. Each of the bores 30, 32, 34 and 36 opens through the nozzle end 26 into the bore of a respective nipple 24 for respective communication with tubes 16, 18, 20 and 22. The opposite ends of the bores 30, 32, 34 and 36 open through the end face 38 and cooperate with the valve structure generally designated by reference character 40, formed intermediate the syringe structure 12 and nozzle structure 14. The syringe structure 12 includes a plunger 42 and plunger tip 44 reciprocally movable within the bore 46 of a cylindrical syringe wall 48.

The nozzle body 28 is mounted within one end of the syringe body 48 so that the radially outer surface of the nozzle body 28 engages the inner cylindrical surface of syringe body 48 with allowance for relative rotation. The conduit end 26 of the nozzle structure 14 has a radially outwardly extending annular flange 50 which axially abuts the end of the syringe body 48 including a radially outwardly extending annular flange 52 having the same outer diameter as the nozzle flange 50. The syringe body 48 has a second outwardly extending flange 54 which is somewhat spaced from the end flange 52 and has the same outer diameter. The flanges 51, 52 and 54 are bridged by a split retainer ring 56 and 58 as more fully described hereinafter.

The syringe body 48 has a radially inwardly extending annular flange 60 which serves as both a retaining wall for the valve structure 40 and as a stop member for the syringe plunger 42. The flange 60 provides a stop formation against which the plunger tip 44 becomes engaged at the end of the syringe discharge stroke The flange 60 includes a central, through aperture 60a and notch 61 extending radially outwardly from the aperture 60a through which fluid is passed to or from the syringe chamber 46. The flange 60 also includes an annular surface 60b facing the nozzle structure 14; an elastic O-ring is seated within an annular groove 60c formed at the outer periphery of the flange face 60b. The O-ring 62 provides a peripheral seal between the flange 60 and the valve disk 64 as further described hereinafter.

The nozzle body 28 includes a cylindrical guide formation 66 concentrically projecting axially from the end face 38. As shown in FIG. 2, the cylindrical guide 66 fits through the central aperture of an elastomeric cushion disk 68 which is seated against the end face 38 of the nozzle body 28. A nozzle valve disk 70 is seated against the cushion disk 68; in order to key the valve disk 70 and cushion disk 68 for rotation with the nozzle body 28, a keying tongue 72 projects axially from the periphery of the end face 38 and passes through respective aligned mortises 68a and 70a. The valve disk 70 also has four through apertures 72, 74, 76 and 78 which are respectively aligned with the nozzle bores 30, 32, 34 and 36 and with one of the corresponding intermediary apertures 80 formed through the cushion disk 68. The syringe valve disk 64 is keyed for joint rotation radially projects into a mortise 64a formed in the periphery of the valve disk 64.

Both of the valve disks 64 and 70 are cast from ceramic material, for example high purity alumina, which can be ground to a highly polished finish enabling the flatness of the engaged surfaces sufficiently conforming so that a fluid-tight seal is maintained between the surfaces even while they are relatively rotated during valve operation. The highly polished finish of the engaged surfaces prevents excessive rotational resistance and frictional forces during the valve operation and the fluid-tight seal which is maintained during the relative rotation prevents any accumulation of fluid between the engaged surfaces which could otherwise cause cross-contamination of the different fluids flowing sequentially through the assembly. High purity alumina is a particularly suitable material for molding and grinding to fabricate the valve disks 64 and 70; preferably their engaged surfaces are ground to be flat within a tolerance of, for example, three (3) light bands with a surface roughness of 15–30 rms. In contrast, the other major components of the assembly 10 can be molded from suitable thermoplastic resins such as polypropylene, polycarbonate and ABS.

In assembling the syringe structure 12, nozzle structure 14 and valve structure 40, the syringe valve disk 64, nozzle valve disk 70, gasket disk 68 and nozzle body 28 are all received within the bore of the syringe body 48. Thereafter the radially inwardly extending flanges 56a (and 58a, not shown) of the respective retainer ring halves 56 and 58 are mounted on the syringe body 48 so that they axially abut the syringe body flange 54; then the ring halves 56 and 58 can be slightly flexed to insert the radially inwardly extending flanges 56b and 58b axially outwardly abutting the nozzle flange 50. The resulting oppositely directly forces applied by the flanges 56a, 58a, and 56b, 58b exert inward pressure on the nozzle which forces a slight compression of the cushion disk 68 and O-ring 62 which oppose the compression with sufficient tension not only to maintain the coupling of the syringe body 48 and nozzle body 28 but also to force the valve disk 64 and 70 into very tight but relatively rotatable engagement.

The ring halves 56 and 58 are themselves coupled by inserting coupling pins 56c projecting from ring half 56 into mating mortises 58c formed in the ring half 58 As best shown in FIG. 1, the coupled ring halves 56 and 58 are keyed to the nozzle structure 14 by a keying tongue 50a which axially projects from the nozzle flange 50 and fits into a slot 56d formed in the retaining ring flange 56b; similar keying 50a, 58d cooperate to ensure that the coupled ring halves 56 and 58 jointly rotate with the nozzle structure 14 and the keyed disks 68 and 70. A knurled rotating collar 82 can then be slid forward from its initial position shown in the exploded perspective of FIG. 1 so that it is "snap-fitted" over and between outward flanges on the split retainer ring halves 56 and 58 to which it is keyed for joint rotation by an axial rib 58e on the ring 58 which fits into an axially extending slot 82a formed in the collar 82. The snap-fit of the collar completes the coupling of the ring halves 56 and 58 and retention of the assembly 10 without welding, bonding, or threaded fasteners in order to promote an inexpensive and disposable assembly.

Figure 3:
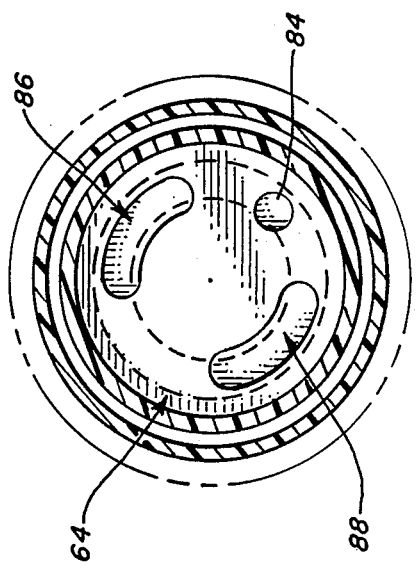
FIG. 3 is a sectional view taken along line 3—3 in FIG. 2 illustrating the arrangement of flow conduits in one of the rotatable valve members.

Referring to FIGS. 2 and 3, the syringe valve disk 64 has a single through bore 84 which is offset from the central axis but is always aligned with the through notch 61 and in communication with syringe chamber 46 through flange aperture 60a promoted by the keying of the valve disk 64 to syringe body 48. The central aperture 60a provides for symmetrically balanced hydraulic pressure exerted against the valve disk 64 by the fluid discharged by the plunger 42 prior to passage of the fluid through the notch 61 into the bore 84. Relative rotation of the syringe body 48 and the rotating collar 82 produces relative rotation between the syringe valve disk 64 and the nozzle valve disk 70 in order to selectively align the syringe valve disk bore 84 with any one of the four nozzle valve disk bores 72, 74, 76 or 78; these bores are always aligned with the respective nozzle bores 30, 32, 34 and 36 and the respective tubes 16, 18, 20, and 22 as provided by the keying of the nozzle valve disk 70 to the nozzle structure 14. As a result of the described relative rotation, the syringe chamber 46 can be aligned for communication with any single one of the tubes 16, 18, 20 and 22 so that the valving action of the valve structure 40 functions as a fluid flow-channel selector.

Figure 5:
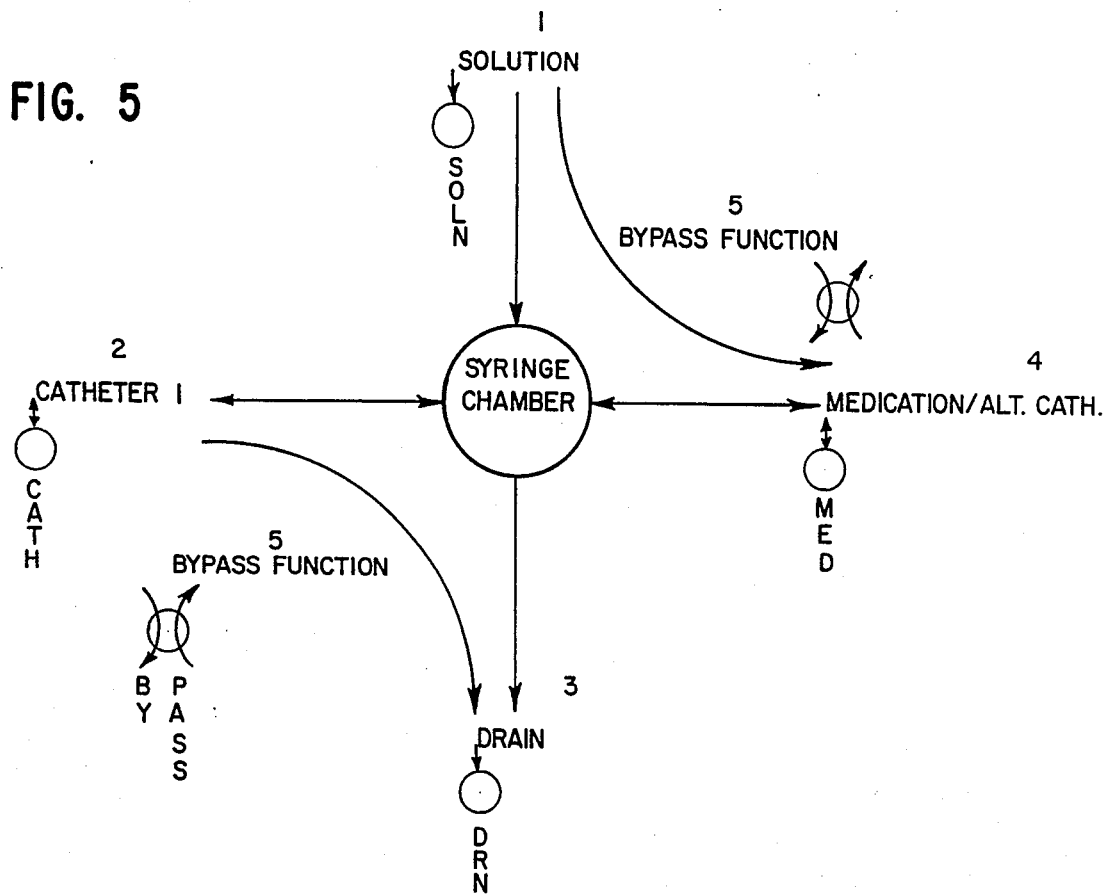
FIG. 5 is a diagrammatic illustration of the multiple fluid flow channels through the assembly created by relative rotation of the valve members.
Figure 7:
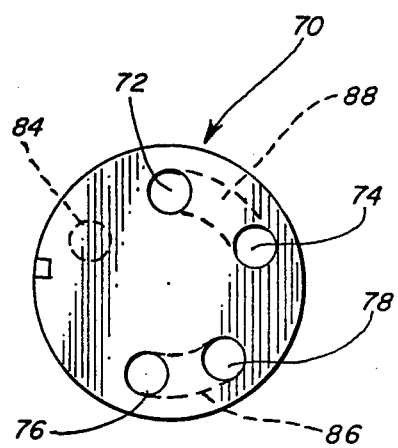
FIG. 7 is a plan view of the relatively rotatable valve members shown in FIGS. 1-3 and illustrating the relative alignment of the flow conduits in the valve members in a position providing for fluid flow through the assembly which bypasses the fluid chamber within the syringe structure.

The syringe valve disk 64 also includes a pair of arcuate, blind slots 86 and 88 which open only through the surface which engages the nozzle valve disk 70; as best shown in FIG. 7, the slots 86 and 88 can be relatively aligned so that each slot provides a flow passage between an adjacent pair of the nozzle valve disk apertures 72, 74 and 76, 78; in this position which is the fifth, bypassed position of the bore 84 as indicated in FIG. 5, the bore 84 is not aligned with any of the four nozzle valve disk apertures, and therefore the syringe chamber 46 is closed to communication with any of the four tubes 16, 18, 20 and 22. The slots 86 and 88 thus function as fluid communication passages between adjacent tube pairs for bypassing communication with the syringe chamber 46. In order to ensure that the bore 84 cannot be aligned with one of the four apertures 72, 74, 76 and 78 when fluid-flow bypassing the syringe chamber 46 is required, these apertures are distributed radially asymmetrically; the arcuate slots 86 and 88 in the syringe valve disk 64 are located for corresponding alignment with the adjacent aperture pairs and nonalignment of the bore 84 with any of the apertures, even though the slots 86 and 88 and the bore 84 are positioned concentrically. By comparison, the fifth position of the bore 84 and the syringe valve disk 64 as a whole, as indicated in FIG. 7, represents a relative rotation of the valve disks 64 and 70 with respect to the position illustrated in FIG. 2 in which the bore 84 is aligned with the nozzle valve disk aperture 78 through which the syringe chamber 46 is in fluid communication with the auxiliary tube 22 (FIG. 1).

FIG. 5 represents the diagrammatic functions in the operation of the illustrated embodiment of the flow control apparatus 10, in which the numerals 1–5 indicate the different relative rotational positions of the bore 84 and the syringe valve disk 64 as a whole with respect to the nozzle valve disk 70 and the functionally labeled tubes as indicated in FIG. 1. In practice, the tubes and the ring 82 to which they are ultimately keyed are maintained rotationally stationary by gripping the collar 82 with the operator's left hand in the orientation of the Q assembly 10 as viewed in FIG. 6; the syringe body 48 is rotated with the right hand, which produces actual rotation of the syringe valve disk 64 with respect to the stationary nozzle valve disk 70.

The operating sequence is described with particular reference to irrigation and drainage of body fluids as typically employed to keep the bladder and its passages free of clots and built-up fluid often following prostate surgery. In position 1, the valve bore 84 is aligned to place the syringe chamber 46 in communication with the solution supply tube 20; withdrawal of the plunger will draw a prescribed amount of solution into the syringe chamber 46. The syringe body 48 and the valve disk 64 can then be rotated into position 2 in which the bore 84 is aligned to communicate the syringe chamber 46 with the catheter tube 16; the plunger 42 is then depressed, facilitated by the finger grip flanges 90, to discharge the solution through the catheter into the organ. Alternatively, the bore 84 can be aligned with the auxiliary tube 22 when used an alternative catheter in rotational position 4. Similarly, fluid can be drawn out of an organ into the syringe chamber 46 through either catheter tube 16 or auxiliary tube 22 when the bore 84 is in either position 2 or position 4, respectively. Thereafter, the bore 84 can be rotated into position 3 and alignment with the drain tube 18, and the plunger 42 can be depressed to discharge the fluid from the syringe chamber 46 to a drain or a sampling container.

When the bore 84 is rotated into the bypass position 5, the bypass slot 86 will interconnect the catheter tube 16 with the drain tube 18 which allows irrigating solution from the organ to flow through the catheter directly into the drain tube 18.

Position 5 also aligns bypass slot 88 to interconnect the solution supply tube 20 with auxiliary tube 22 enabling, for example, a medication drip to flow directly into an alternative catheter for which the auxiliary tube can be employed.

Figure 6:
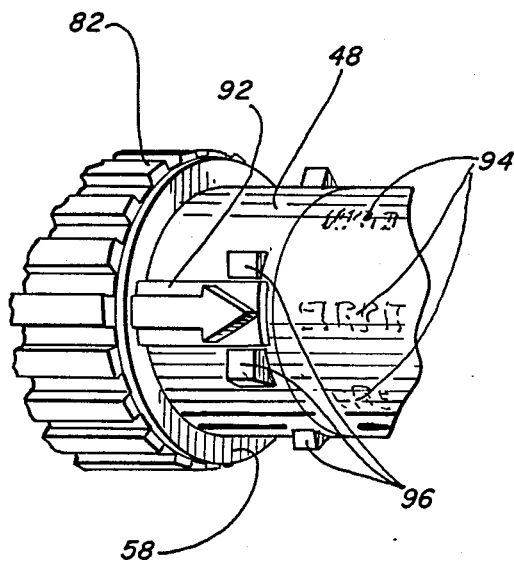
FIG. 6 is a fragmentary, perspective view of a rotatable channel indicator shown in FIG. 1.

Referring to FIG. 6, the retainer ring half 58 (or alternatively half 56) has an axially projecting tab 92 carrying an indicia arrow which points toward one of the five valve position identification labels 94 applied on the syringe body 48. The syringe body 48 also has a plurality of outwardly projecting detents 96 with which the tab 92 is selectively engageable in a snapping action upon relative rotation of the syringe body 48 and the retaining ring half 58; the detents 96 not only direct the arrow toward the correct valve indication label 94 but also maintain the tab 92, and therefore the attached retaining ring 58 and all of the nozzle structure 14 keyed thereto, in the selected relative position of the valve disks 64 and 70 which is indicated by the respective label 94.

The multiple conduits of the nozzle structure 14 and the convenient rotational channel selection combined with capability for bypassing the syringe chamber provide particularly flexible employment of the flow control apparatus in various organ treatments requiring different fluid flow sequences.

While a preferred embodiment of the invention is illustrated and described, it is envisioned that those skilled in the art may devise various modification once possessed of this disclosure. Accordingly, the invention is to be defined by the spirit and scope of the claims appended hereto, and is not limited to the specific embodiment described.

The invention is claimed as follows:

1. A flow control apparatus for providing selective fluid communication with physiological organs, comprising: a nozzle structure including a plurality of discrete ports for connection to a corresponding plurality of separate fluid conduits; syringe means having a fluid chamber for containing and discharging fluid in communication with at least one of said conduits; two valve members having respective engaged surfaces relatively rotatable to provide valving action, said valve members including a first valve member having a plurality of through apertures respectively communicating with said nozzle ports and a second valve member having a through passageway communicating with said syringe chamber, said valve members being further selectively adjustable relative to at least one of said apertures to enable fluid flow between said respective nozzle ports and said syringe chamber; and clamp means for applying axially directed opposing forces on said valve members in order to establish a fluid-tight seal between said engaged surfaces; wherein said syringe means includes a cylindrical syringe body housing said chamber, said body further housing said valve members.

2. The flow control apparatus according to claim 1 wherein said syringe body includes generally annular internal wall between said syringe chamber and said valve members.

3. The flow control apparatus of claim 2 wherein said internal wall is defined by an annular flange having a central aperture providing said communication of said syringe chamber with said passageway through said second valve member.

4. The flow control apparatus according to claim 2 wherein said second valve member and said internal wall are at least partially separated by sealing means for providing fluid-tight seal therebetween.

5. The flow control apparatus according to claim 4 wherein said sealing means comprises a resilient O-ring.

6. A flow control apparatus for providing selective fluid communication with physiological organs, comprising: a nozzle structure including a plurality of discrete ports for connection to a corresponding plurality of separate fluid conduits; syringe means having a fluid chamber for containing and discharging fluid in communication with at least one of said conduits; two valve members having respective engaged surfaces relatively rotatable to provide valving action, said valve members including a first valve member having a plurality of through apertures respectively communication with said nozzle ports and a second valve member having a through passageway communicating with said syringe chamber, said value members being selectively adjustable relative to at least one of said apertures to enable fluid flow between said respective nozzle port and said syringe chamber; and clamp means for applying axially directed opposing forces on said valve members in order to establish a fluid-tight seal between said engaged surfaces; wherein said claim means comprises cushion means for resiliently exerting said opposing forces on said respective valve members; and wherein said cushion means comprises a resilient member engaging said first valve member and having a plurality of through passageways in fluid communication with said respective apertures.

7. The flow apparatus according to claim 1 wherein said nozzle structure is jointly rotatable with said first valve member and said syringe means is jointly rotatable with said second valve member.

8. The flow control apparatus according to claim 1 wherein both of said valve members are fabricated from ceramic material, each of said engaged surfaces being ground and polished to enable said fluid-tight sealing therebetween.

9. A flow control apparatus for providing selective fluid communication with physiological organs, comprising: a nozzle structure including a plurality of discrete ports for connection to a corresponding plurality of separate fluid conduits; syringe means having a fluid chamber for containing and discharging fluid in communication with at least one of said conduits; two valve members having respective engaged surfaces relatively rotatable to provide valving action, said valve members including a first valve member having a plurality of through apertures respectively communicating with said nozzle ports and a second valve member having a through passageway communicating with said syringe chamber, said valve members being selectively adjustable relative to at least one of said apertures to enable fluid flow between said respective nozzle port and said syringe chamber; and clamp means for applying axially directed opposing forces on said valve members in order to establish a fluid-tight seal between said engaged surfaces; wherein said second valve member comprises flow passage means for selectively interconnecting at least two of said apertures through said first valve member in order to enable fluid flow bypassing said syringe chamber.

10. A flow control apparatus for providing selective fluid communication with physiological organs comprising: a nozzle structure including a plurality of discrete ports for connection to a corresponding plurality of separate fluid conduits; syringe means having a fluid chamber for containing and discharging fluid in communication with at least one of said conduits; two valve members having respective engaged surfaces relatively rotatable to provide valving action, said valve members including a first valve member having a plurality of through apertures respectively communicating with said nozzle ports and a second valve member having a through passageway communicating with said syringe chamber, said valve members being selectively adjustable relative to at least one of said apertures to enable fluid flow between said respective nozzle port and said syringe chamber; and clamp means for applying axially directed opposing forces on said valve members in order to establish a fluid-tight seal between said engaged surfaces; wherein said syringe means comprises a cylindrical body housing said fluid chamber, and wherein one end of said cylindrical body is closed by said nozzle structure.

11. The flow control apparatus according to claim 10 wherein said nozzle structure comprises an annular flange engaged against said end of said body.

12. The flow control apparatus according to claim 11 wherein at least a portion of said nozzle structure is removably received within said cylindrical body.

13. The flow control apparatus according to claim 11 wherein said body comprises a radially outwardly extending annular flange, and wherein said clamp means comprises means for directing said opposing forces respectively upon said nozzle structure flange and said body flange in order to communicate said axially directed opposed forces on said valve members.

14. The flow control apparatus according to claim 13 wherein said clamp means comprises first and second clamp members respectively directing said opposing forces upon said nozzle structure flange and said body flange in order to communicate said opposing forces onto said respective valve members.

15. The flow control apparatus according to claim 14 wherein said clamp means further comprises retaining means for retaining said clamp members in engagement with said first and second flanges.

16. A flow control apparatus for providing selective fluid communication with physiological organs, comprising: a nozzle structure including a plurality of discrete ports for connection to a corresponding plurality of separate fluid conduits; syringe means having a fluid chamber for containing and discharging fluid in communication with at least one of said conduits; two valve members having respective engaged surfaces relatively rotatable to provide valving action, said valve members including a first valve member having a plurality of through apertures respectively communicating with said nozzle ports and a second valve member having a through passageway communicating with said syringe chamber, said valve member being further selectively adjustable relative to at least one of said apertures to enable fluid flow between said respective nozzle ports and said syringe chamber; and clamp means comprising first and second cushion means for resiliently exerting axially directed opposing forces on said valve members in order to establish a fluid-tight seal between said engaged surfaces.

17. The flow apparatus according to claim 16 wherein said nozzle structure is jointly rotatable with said first valve member and said syringe means is jointly rotatable with said second valve member.

18. The flow control apparatus according to claim 16 wherein both of said valve members are fabricated from ceramic material.

19. The flow control apparatus according to claim 16 wherein said second valve member comprises flow passage means for selectively interconnecting at least two of said apertures through said first valve member in order to enable fluid flow bypassing said syringe chamber.

20. A flow control apparatus for providing selective fluid communication with physiological organs, comprising: a nozzle structure including a plurality of discrete ports for connection to a corresponding plurality of separate fluid conduits; syringe means having a fluid chamber for containing and discharging fluid in communication with at least one of said conduits; two valve members having respective engaged surfaces relatively rotatable to provide valving action, said valve members including a first valve member having a plurality of through apertures respectively communicating with said nozzle ports and a second valve member having a through passageway communicating with said syringe chamber, said valve members being further selectively adjustable relative to at least one of said apertures to enable fluid flow between said respective nozzle ports and said syringe chamber; and clamp means comprising first and second cushion means for resiliently exerting axially directed opposing forces on said valve members in order to establish a fluid-tight seal between said engaged surfaces; wherein said syringe means comprises a cylindrical body housing said fluid chamber and said valve members, and wherein one end of said cylindrical body is closed by said nozzle structure.

21. The flow control apparatus according to claim 20 wherein said nozzle structure comprises an annular flange engaged against said end of said body.

22. The flow control apparatus according to claim 21 wherein at least a portion of said nozzle structure is removably received within a bore formed in said cylindrical body.

23. The flow control apparatus according to claim 21 wherein said body comprises a radially outwardly extending annular flange, and wherein said clamp means comprises means for directing said opposing forces respectively upon said nozzle structure flange and said body flange in order to communicate said axially directed opposing forces on said valve members.

24. The flow control apparatus according to claim 23 wherein said clamp means comprises first and second clamp members respectively directing said opposing forces upon said nozzle structure flange and said body flange in order to communicate said opposing forces onto said respective valve members.

25. The flow control apparatus according to claim 24 and further including retaining means for retaining said clamp members engaged with the first and second flanges.

26. A flow control apparatus for providing selective fluid communication with physiological organs, comprising: nozzle structure including a plurality of discrete ports for connection to a corresponding plurality of separate fluid conduits; syringe means having a fluid chamber for containing and discharging fluid in communication with at least one of said conduits; two valve members having respective engaged surfaces relatively rotatable to provide valving action, said valve members including a first valve member having a plurality of through apertures respectively communicating with said nozzle ports and a second valve member having a through passageway communicating with said syringe chamber, said valve members being further selectively valve members adjustable relative to at least one of said apertures to enable fluid flow between said respective nozzle ports and said syringe chamber; said syringe means including a cylindrical body housing said syringe chamber, both of said valve members and at least a portion of said nozzle structure, said valve members and said nozzle structure portion being secured within said body by a a pair of clamping members seated circumferentially on said body and on said nozzle structure retaining means for coupling said clamping members thereabout.

27. The flow control apparatus according to claim 26 wherein both of said valve members are fabricated from ceramic material, each of said respective engaged surfaces being ground and polished to enable fluid-tight sealing therebetween.

28. The flow control apparatus according to claim 27 wherein said clamping members are configured and arranged for applying axially-directed opposing forces on said valve members in order to establish said fluid-tight seal between said engaged surfaces.

29. The flow control apparatus according to claim 28 wherein said nozzle structure comprises an annular flange extending radially outwardly with respect to said syringe body, said syringe body including a radially outwardly extending annular flange, and wherein said clamping members include first and second clamp flanges formed at opposing ends thereof and respectively seated upon said nozzle structure flange and said syringe body flange.

30. The flow control apparatus according to claim 29 wherein said nozzle structure is jointly rotatable with said first valve member and said syringe means is jointly rotatable with said second valve member.

* * * * *